United States Patent

Brautigan et al.

[11] Patent Number: 5,948,985
[45] Date of Patent: Sep. 7, 1999

[54] METHOD AND APPARATUS FOR ULTRASONIC TESTING OF ALUMINUM BILLET

[75] Inventors: David R. Brautigan, Wheeling, W. Va.; Charles D. Merckle, New Matamoras, Ohio

[73] Assignee: Ormet Corporation, Wheeling, W. Va.

[21] Appl. No.: 08/866,817

[22] Filed: May 30, 1997

Related U.S. Application Data

[60] Provisional application No. 60/018,774, May 31, 1996.

[51] Int. Cl.⁶ .......................... G01N 29/10; G01N 29/26
[52] U.S. Cl. .................................. 73/622; 73/641; 73/634
[58] Field of Search ............................ 73/622, 644, 641, 73/620, 625, 633, 634, 635, 636, 637, 638

[56] References Cited

U.S. PATENT DOCUMENTS

| | | | |
|---|---|---|---|
| Re. 30,926 | 5/1982 | Ross et al. | 73/638 |
| 2,956,185 | 10/1960 | von Stocker | 310/8.7 |
| 3,233,449 | 2/1966 | Harmon | 73/67.8 |
| 3,371,524 | 3/1968 | Wloszek | 73/622 |
| 3,382,707 | 5/1968 | Heselwood | 73/71.5 |
| 3,687,219 | 8/1972 | Langlois | 181/0.5 R |
| 3,763,695 | 10/1973 | Zeiters | 73/71.5 U |
| 3,798,961 | 3/1974 | Flambard et al. | 73/71.5 |
| 4,033,178 | 7/1977 | Holt et al. | 73/71.5 |
| 4,099,418 | 7/1978 | Bennett et al. | 73/622 |
| 4,100,809 | 7/1978 | Bobrov et al. | 73/638 |
| 4,195,530 | 4/1980 | Ross et al. | 73/644 |
| 4,297,886 | 11/1981 | Anikeev et al. | 73/642 |
| 4,312,230 | 1/1982 | Bricker et al. | 73/638 |
| 4,328,708 | 5/1982 | Bagwell | 73/622 |
| 4,423,636 | 1/1984 | Plante | 73/622 |
| 4,472,975 | 9/1984 | Beck et al. | 73/644 |
| 4,563,900 | 1/1986 | Harada et al. | 73/644 |
| 4,566,333 | 1/1986 | Chubachi et al. | 73/642 |
| 4,587,849 | 5/1986 | Gross | 73/644 |
| 4,599,900 | 7/1986 | Friedman | 73/622 |
| 4,718,277 | 1/1988 | Glascock | 73/622 |
| 4,796,632 | 1/1989 | Boyd et al. | 128/662.03 |
| 4,813,402 | 3/1989 | Reichenberger et al. | 108/24 |
| 4,843,884 | 7/1989 | House et al. | 3/622 |
| 4,868,798 | 9/1989 | Fasnacht, Jr. et al. | 73/634 |
| 4,924,707 | 5/1990 | Kliesch | 73/644 |
| 5,001,932 | 3/1991 | Light et al. | 73/644 |
| 5,007,291 | 4/1991 | Walters et al. | 73/640 |
| 5,097,710 | 3/1992 | Palynchuk | 73/644 |
| 5,113,697 | 5/1992 | Schlawne | 73/602 |
| 5,235,856 | 8/1993 | Cueman et al. | 73/622 |
| 5,279,160 | 1/1994 | Koch | 74/643 |
| 5,313,837 | 5/1994 | Haynes | 73/622 |
| 5,343,109 | 8/1994 | Möckl | 310/334 |
| 5,373,743 | 12/1994 | Abrahams | 73/644 |
| 5,406,851 | 4/1995 | Li | 73/644 |
| 5,419,195 | 5/1995 | Quinn | 73/623 |
| 5,426,980 | 6/1995 | Smith | 73/644 |
| 5,454,269 | 10/1995 | Vogt | 73/644 |
| 5,469,744 | 11/1995 | Patton et al. | 73/644 |
| 5,473,943 | 12/1995 | Schoenen et al. | 73/644 |

*Primary Examiner*—Michael Brock
*Assistant Examiner*—Rose M. Miller
*Attorney, Agent, or Firm*—Webb Ziesenheim Logsdon Orkin & Hanson, P.C.

[57] ABSTRACT

An ultrasonic inspection apparatus and method tests elongated, cylindrical aluminum billets. The apparatus includes a frame supporting a movable carriage having at least one ultrasonic detector assembly mounted thereon. Each ultrasonic detector assembly includes a bracket detachably mounted to the carriage, at least one holder movably coupled to the bracket, a spring-biasing mechanism to bias the holder from the bracket, a transducer shoe attached to the holder and a transducer attached to the shoe. The shoe is configured to conform to the outer surface of the billet and to be flooded with fluid to assist in testing.

10 Claims, 7 Drawing Sheets

METHOD AND APPARATUS FOR ULTRASONIC TESTING OF ALUMINUM BILLET

This application claims the benefit of U.S. Provisional Application Ser. No. 60/018,774 filed May 31, 1996 entitled "Method and Apparatus for Ultrasonic Testing of Aluminum Billet."

BACKGROUND OF THE INVENTION

The present invention relates generally to non-destructive testing of elongated cylindrical workpieces, and more particularly, to methods and apparatus for ultrasonically inspecting as-cast aluminum billet. Heretofore, in the non-destructive testing of elongated, large or bulky parts by ultrasonic inspection techniques, the part or test piece to be inspected has been submerged within a fluid bath, such as water, and a transducer is caused to scan from one end to the other of the part. The construction and maintenance of large tanks for containing the water and for submersion of the test piece is problematic as well as expensive. In other prior art techniques, the ultrasonic transducer inspection head remains stationary while the workpiece is moved longitudinally along its axis to conduct the inspection. In cases where the workpiece is very long, the plant space required for conducting such an inspection is, likewise, extremely long. This also causes problems in plant design and operation.

A further problem is encountered in inspecting as-cast billet due to the naturally occurring surface irregularities found along the surface of the billet. Generally, such-as cast parts or shapes are inspected while submerged in a coupling fluid to provide the necessary coupling between the transducer and the irregular surface of the test piece. The present invention solves this problem by providing a special transducer shoe design to permit ultrasonic inspection without submerging the test billet while still obtaining excellent ultrasonic coupling at relatively high inspection speeds.

The present invention also provides an ultrasonic inspection machine in which the test piece is stationary and the ultrasonic transducer heads are movable to provide an inspection machine which occupies much less plant floor space than known billet inspection devices. These as well as other features and attributes of the invention will become more apparent when the appended drawings are studied in conjunction with the following description.

SUMMARY OF THE INVENTION

Briefly stated, the present invention is directed to an ultrasonic billet inspection apparatus and method for ultrasonically inspecting as-cast cylindrical billet of various diameter (upwards of 15" in diameter) and having a length on the order of about 25'. The inspection apparatus includes first and second pairs of axially spaced rolls for supporting the billet and includes means for selectively rotating the billet to be tested in 90° increments. The first and second pairs of support rolls are vertically movable to facilitate pick-up of the billet to be inspected from a pair of mill table beams or loading rails positioned transverse to the centerline of the apparatus. The loading rails permit the billet to be rolled onto the inspection apparatus and the first and second pairs of support rolls are then raised to engage the surface of the billet adjacent to the opposed ends thereof. The billet is lifted by the rolls from the loading rails and brings the billet into alignment beneath the ultrasonic inspection portion of the apparatus. The ultrasonic inspection portion of the apparatus includes a horizontally extending bridge beam and a trolley assembly movably attached to the bridge beam and axially aligned above the billet and support rolls. The trolley member has a length equal to about one-half the length of the billet and includes wheeled attachment bracket means to permit the trolley to move along the bridge beam. The trolley member carries a pair of ultrasonic flaw detectors mounted at each end thereof. Each of the pair of ultrasonic flaw detecting means comprises a pair of transducers, spring-mounted on a fixture which is detachably secured to the trolley. The mounting fixtures are easily detached from the trolley to accommodate inspection of various billet diameters. The fixture positions each of the transducers at a 90° angle relative to one another and aligned perpendicular to the test billet. The transducer mounting fixture also includes a guide wheel assembly positioned intermediate the two spring-loaded transducers to maintain the transducers in an evenly loaded manner against the surface of the billet as the guide wheel rotatably engages the billet surface while the trolley moves along the bridge beam. The mounting fixtures are generally "C"-shaped and carry offset, wing-like arms for mounting the transducers and to axially offset the transducers relative to the longitudinal axis of the billet so that acoustic interference is avoided between the transducers of each pair.

The transducers each include a holder or coupling shoe having a curved face which approximates the curvature of the cylindrical billet being inspected. The shoes are rigid and wear-resistant and preferably are made from an ultra high molecular weight polyethylene material. As alluded to above, the mounting fixtures for holding the pair of ultrasonic flaw detectors include detachment means to permit replacement of the fixture with a new fixture carrying transducer shoes of other curvatures and transducer spacings to accept various billet diameters such as, for example, 9" diameter, 11" diameter, and 15" diameter billet.

Each of the transducer shoes has an undercut region surrounding the soundemitting end of the transducer and includes means for supplying a coupling liquid, such as water, to the undercut region which forms a reservoir to contain the water to provide acoustic coupling between the transducer and the irregular surface of the as-cast billet. The spring-loaded fixtures and guide wheel maintain the transducer shoes in close contact with the billet as the shoes slide along the surface to contain the fluid in the undercut reservoir so as to insure constant acoustic coupling between the transducers and the billet, even though a non-uniform surface may exist on the billet by virtue of its as-cast condition. The undercut reservoir and spring-loaded shoes permit longitudinal movement of the transducer at relatively high inspection speeds, for example, on the order of 6–10" per second, without losing good acoustic coupling with the billet.

The billet inspection machine also includes means, preferably in the form of a hydraulic cylinder, for downwardly moving the lower portion of the trolley carrying the two pairs of ultrasonic flaw detecting means as the first and second pairs of support rolls move vertically upward for engagement of the transducer shoes with the surface of the billet to be inspected. Motor means, preferably in the form of a ball screw assembly, including a telescoping drive shaft and sleeve, move the trolley in two directions along the bridge beam. When moved in a first direction, the first pair of ultrasonic flaw detecting transducers start at a first end of the billet and longitudinally traverse the surface of billet from the first end to its mid-point. Simultaneously with the movement of the first pair of flaw detecting transducers, the second pair of ultrasonic flaw detecting transducers commences at the mid-point of the billet and longitudinally traverses the surface of the billet from its mid-point to its second end as the trolley moves along the bridge beam in the first direction. Thus, the complete length of the billet is ultrasonically inspected by moving the trolley only one-half the length of the billet. Conventional electronic means are employed to signal the operator when defects are detected in the billet. The ends of the billet are also marked where the casting porosity ends so that the billet ends may be sawed off and discarded.

A pair of axially spaced-apart, photoelectric eyes and appropriate limit switches are positioned outboard of each of the pairs of ultrasonic flaw detecting transducers. As the trolley approaches an end of the billet, the first of the photoelectric eyes of the pair senses the end of the billet to slow the trolley motor and the second photoelectric eye then senses the end of the billet to signal the motor to stop and to cause the motor, when again activated, to rotate in a reverse mode to move the trolley in an opposite direction. The device is also equipped with means, preferably in the form of an air cylinder device and cam means, to turn one of the support rolls 90° to permit incremental rotation of the billet for inspection of four quadrants of the billet if needed. A water collection tray is preferably positioned beneath the support rolls having a length approximately that of the billet to collect the coupling fluid as it flows from the transducer shoes. Water may be employed as a coupling fluid during such times as the ambient temperature remains above freezing. When operating at sub-freezing ambient temperatures, an antifreeze additive may be mixed with the water in which case the coupling fluid may be recycled for reuse.

Additional advantages of the present invention will be clarified in the detailed description of the invention wherein like reference numerals represent like elements throughout.

DETAILED DESCRIPTION OF THE INVENTION

Figure 1A:
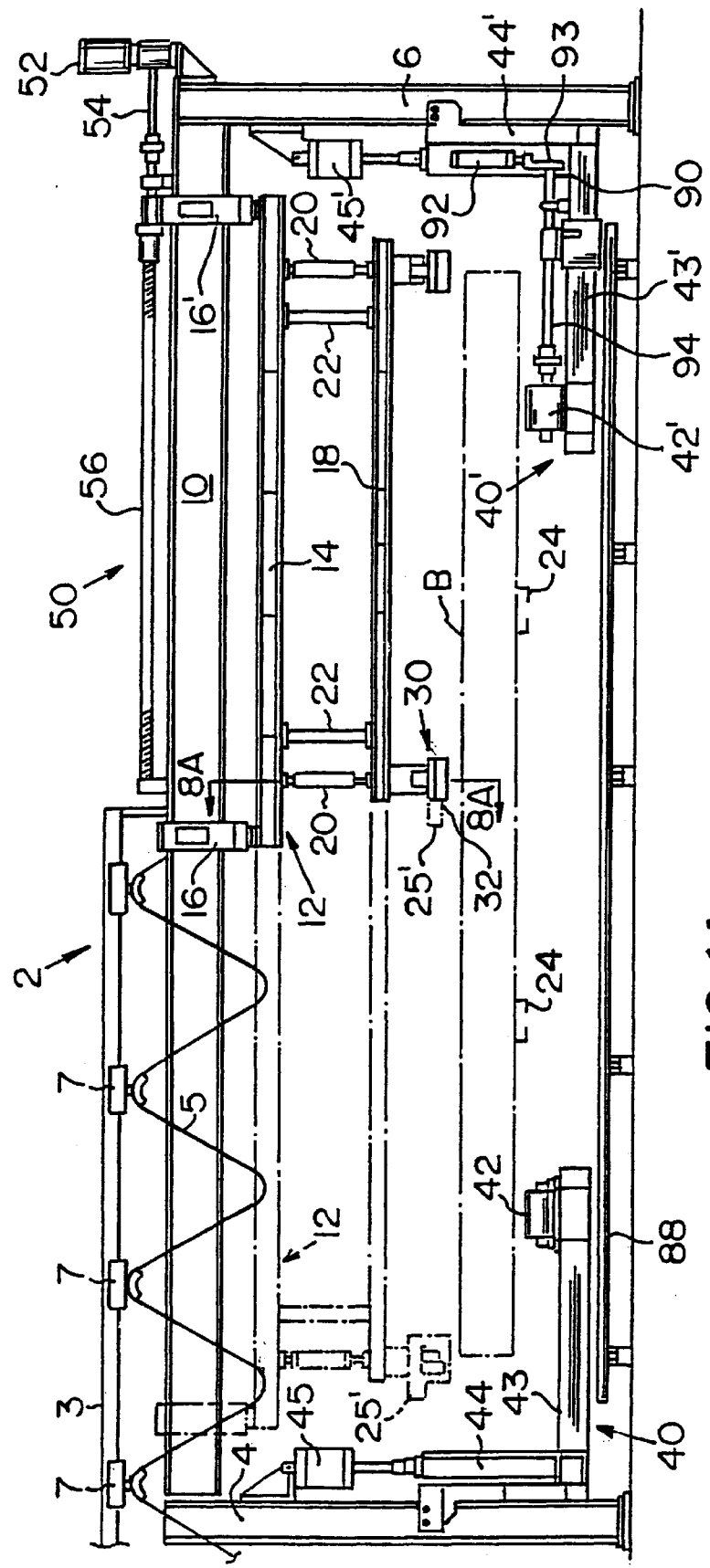
FIG. 1A is a side elevation view of the ultrasonic inspection apparatus of the present invention.
Figure 1B:
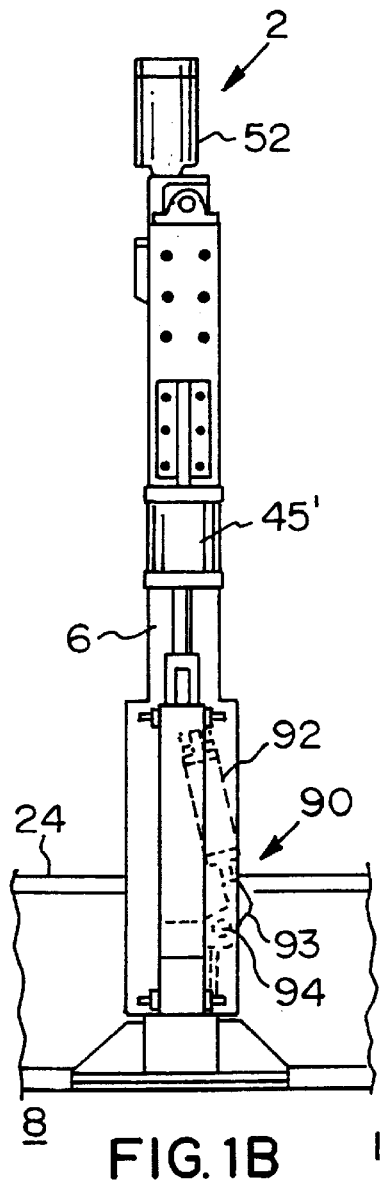
FIG. 1B is a cross sectional end elevation view of the billet inspection apparatus of the present invention taken along section line "B—B" of FIG. 1A.

The ultrasonic billet inspection apparatus of the present invention is identified generally by reference numeral 2 in FIG. 1A. Apparatus 2 comprises two steel end posts 4 and 6, mounted on the floor 8, and interconnected by a horizontally extending bridge beam 10. A trolley assembly 12 is movably attached to the bridge beam 10 for travel between the end posts 4 and 6. A festoon beam 3 extends above the left-hand or west side portion of the bridge beam 10 to supply electric power, water, air and/or hydraulic fluid to the movable trolley assembly 12, as will be explained in greater detail hereinafter. The hoses and wires 5 are looped on movable carriers 7 which move along the festoon beam 3. A billet "B" shown in phantom lines is manually rolled onto the apparatus 2 for inspection by way of a pair of beams or rails 24, also shown in FIG. 2A. Two pairs of billet support roll assemblies 40 and 40' are positioned at opposed ends of the apparatus carrying rollers 42 and 42' which, when raised as in FIGS. 2B and 2C, lift the billet B from the support rails 24 to an inspection position. The rollers 42 are carried by a horizontal cantilever beam 43 attached to a vertically extending beam 44 which is vertically movable by way of a hydraulically actuated cylinder 45 along the end post 4. The support roll assembly 40' includes a horizontal cantilever beam 43' attached to a vertically extending beam 44' which is likewise vertically movable adjacent the end post 6 by actuation of the hydraulic cylinder 45' in a similar manner.

The trolley assembly 12 comprises an upper trolley carrier member 14 in the form of an elongated beam having attachment brackets 16 and 16' which movably engage the bridge beam 10 for travel therealong. The trolley 12 also includes a lower trolley carrier 18 which is attached to the upper carrier 14 by way of a pair of hydraulic or pneumatic cylinders 20 and 20' and telescoping alignment rods/sleeves 22 and 22'. The attachment brackets 16 and 16' of the trolley assembly 12 have internal roller cams 17 and 19 for engaging the web 11 and flange 13', respectively. The lower trolley carrier beam 18 also carries a pair of ultrasonic inspection transducer heads 30 and 30' affixed at either end thereof which will be explained in greater detail hereinafter.

The trolley 12 is moved along the bridge beam 10 by way of a motorized trolley drive system generally designated 50. The drive system 50 includes an AC motor, for example, a three horsepower motor 52, having an appropriate speed reducer 53 for rotating a shaft 54 which moves a ball screw device 55 along a threaded ball screw shaft 56 having, for example, a 3" outside diameter and a 1.5" lead ball screw. In operation, rotation of the shaft 54 causes the ball screw 55 to travel along the ball screw shaft 56 and move the attached trolley carriers 16 and 16' along the bridge beam 10 to the left-hand position shown in phantom lines on FIG. 1. Reverse rotation of the shaft of the ball screw causes the trolley to move in a reverse direction along the bridge beam 10.

Figure 1C:
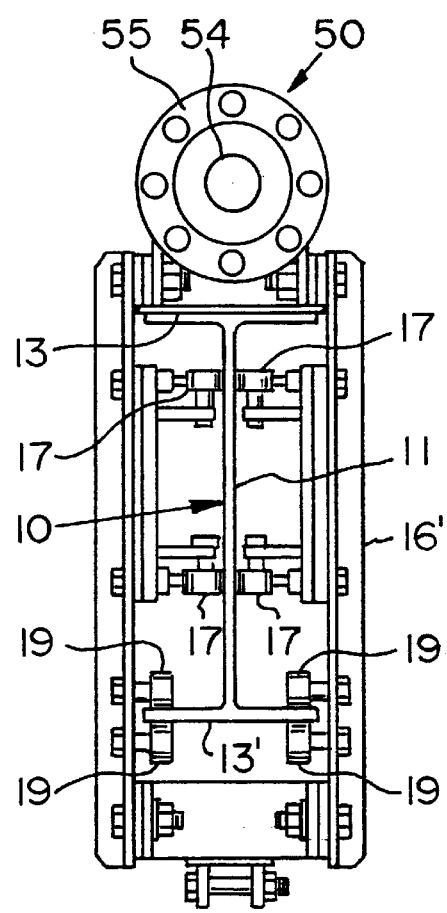
FIG. 1C is a cross sectional view of the ball screw drive shaft, trolley attachment bracket and bridge beam of the present invention taken along section line "C—C" of FIG. 1A.
Figure 1D:
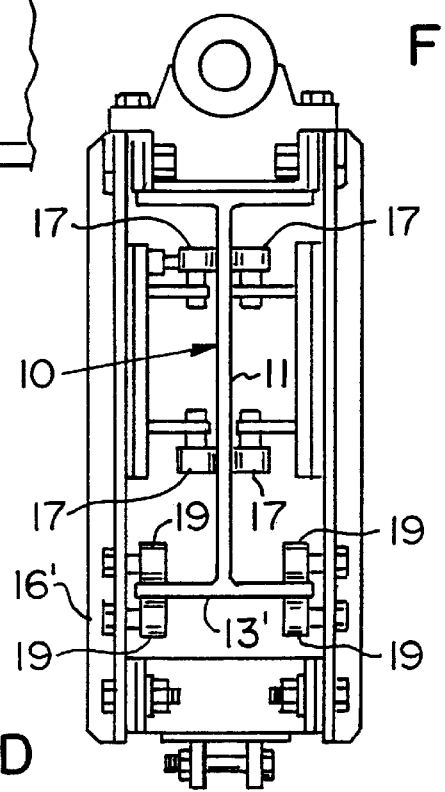
FIG. 1D is a cross sectional view similar to FIG. 1C but taken along section line "D—D" of FIG. 1A.
Figure 1E:
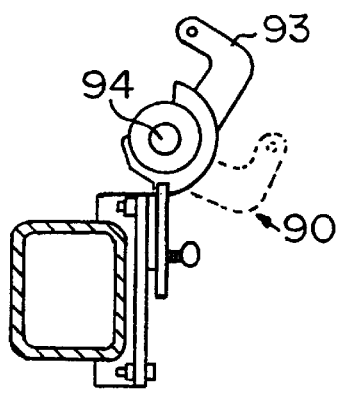
FIGS. 1E–1G are cross sectional views of the billet rotation shaft and cam showing the cam operation for 9" diameter billets, 11" diameter billets and 15" diameter billets, respectively.
Figure 1F:
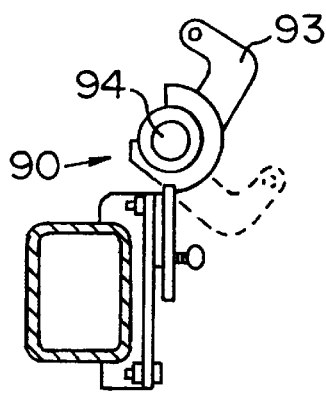
Figure 1G:
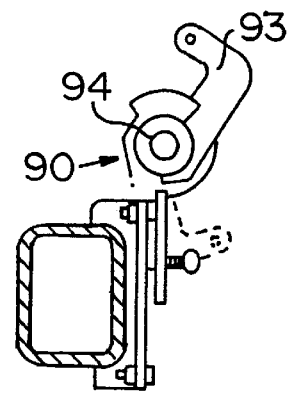
Figure 11:
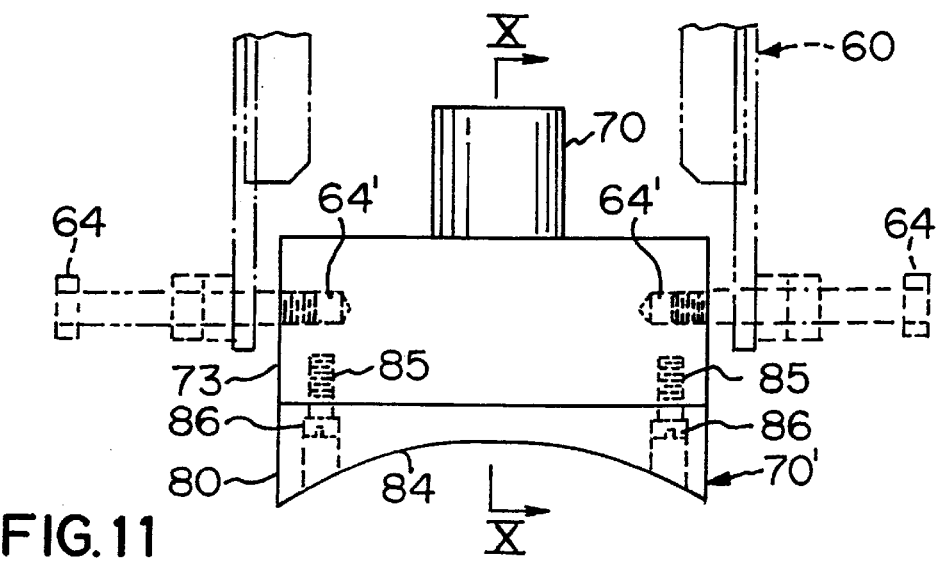
FIG. 11 is an end elevation view of the transducer holder assembly.
Figure 12:
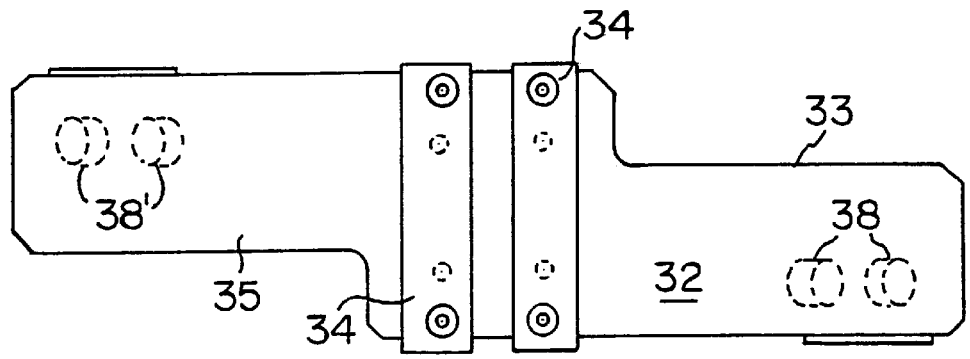
FIG. 12 is a plan view of a fixture for holding a pair of transducers.
Figure 13:
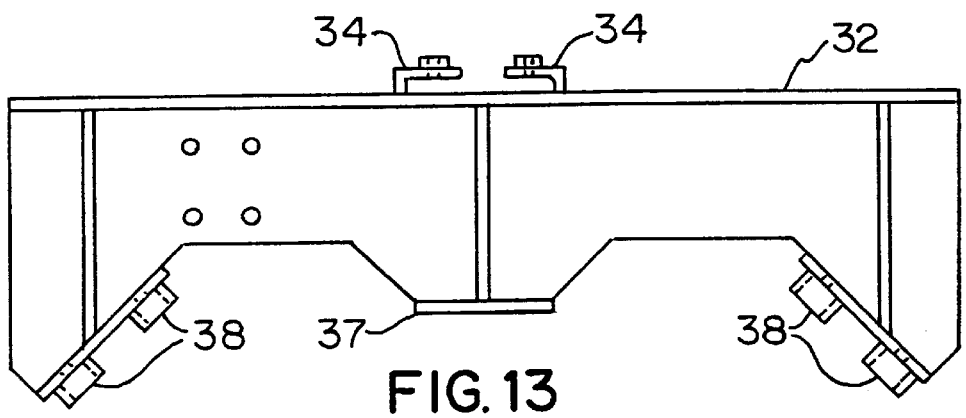
FIG. 13 is a side elevation view of the fixture of FIG. 12.
Figures 14, 15:
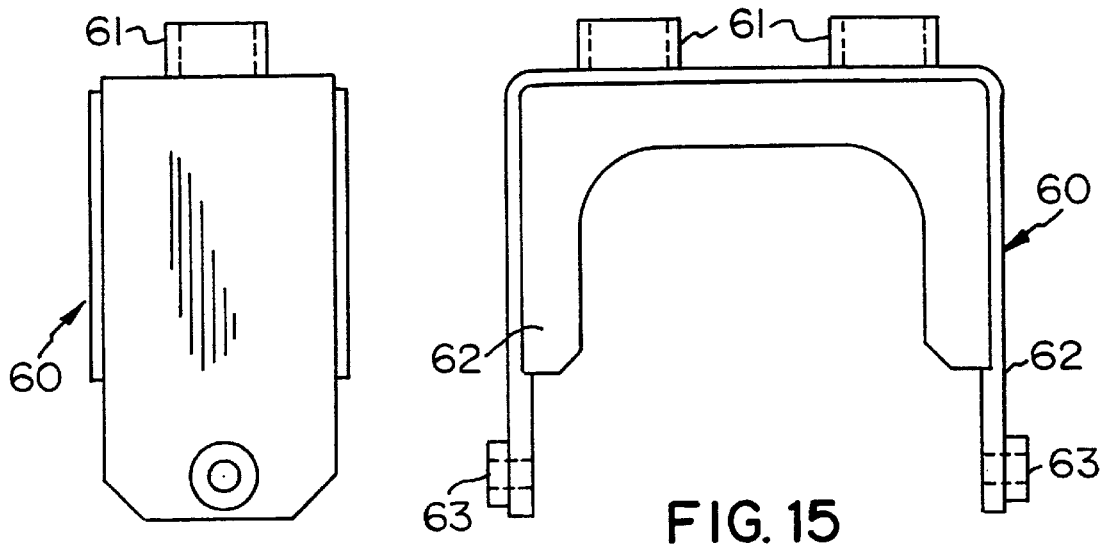
FIG. 14 is an end elevation view of a yoke holder for the transducer assembly for mounting to the fixture of FIGS. 12 and 13.
FIG. 15 is a side elevation view of the yoke holder of FIG. 14.
Figure 16:
FIG. 16 is a side elevation view of a bolt for mounting the transducer assembly to the yoke holder of FIGS. 14 and 15.

As seen in FIGS. 1C and 1D, the bridge beam 10 has a vertical web 11 which joins the upper and lower horizontal flanges 13 and 13', respectively. The pair of ultrasonic flaw detectors generally designated 30 and 30' are detachably affixed to opposed ends of the lower trolley carrier beam 18. The ultrasonic flaw detectors 30, 30' include detachable brackets 32 shown in FIGS. 3A–3C and FIGS. 12 and 13. Each detachable bracket 32 has axially offset wing portions 33 and 35 shown in FIG. 12. The bracket 32 also includes upper mounting angles 34 and 34' which are adapted to slidably engage a lower flange carried by the lower trolley carrier beam 18. Wing bolts 31 shown in FIG. 3A fit within the threaded bores 36 shown in FIG. 13 to lockably engage each bracket 32 on the lower trolley beam 18. The bracket 32 also includes a lower mounting plate 37, FIG. 13, for receiving a guide wheel 39 shown in FIG. 3A. The outer ends of the offset wings 33 and 35 carry outwardly extending pipe shaped sleeves or bushings 38 and 38', respectively. A transducer holder 60 depicted in FIGS. 14 and 15 also carries similar pipe-shaped bushings 61 similar to the sleeve-type bushings 38 carried by the brackets 32. Coil springs 51 positioned over the ends of each of the bushing sleeves 61 and 38, 38', shown in FIG. 3A, along with appropriate bolts and nuts are used to mount the holder 60 to the bracket wings 33 and 35. The holders 60, once mounted, are then permitted to move in a springloaded manner toward the brackets 32. The holders 60 have opposed arms 62 which carry a threaded hole 63 at the ends thereof, see FIGS. 14 and 15. A bolt 64 shown in FIG. 16 is threadably secured through the hole 63 in the holder 60 to pivotally mount a transducer holder assembly 70' shown in FIGS. 10 and 11. Thus, the transducers are mounted in a gimbaled manner.

Figure 3A:
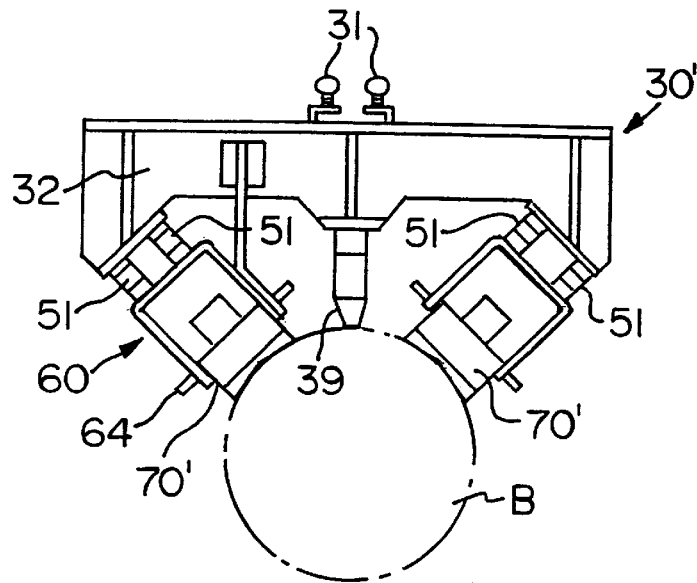
FIGS. 3A–3C are partial end views of the ultrasonic inspection transducers of the present invention and fixture for holding same for various size diameter billets.
Figure 3B:
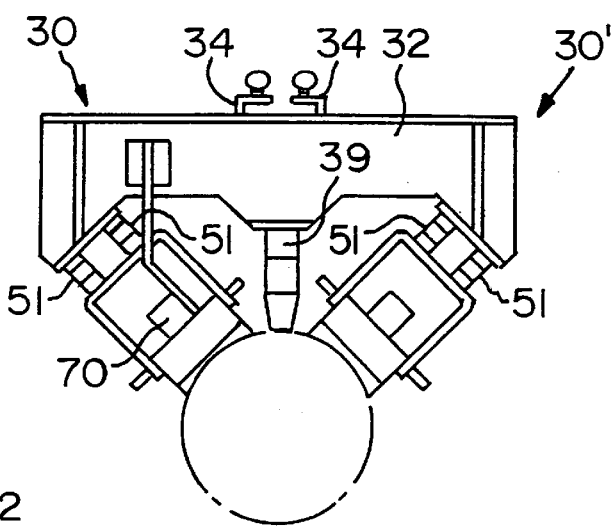
Figure 3C:
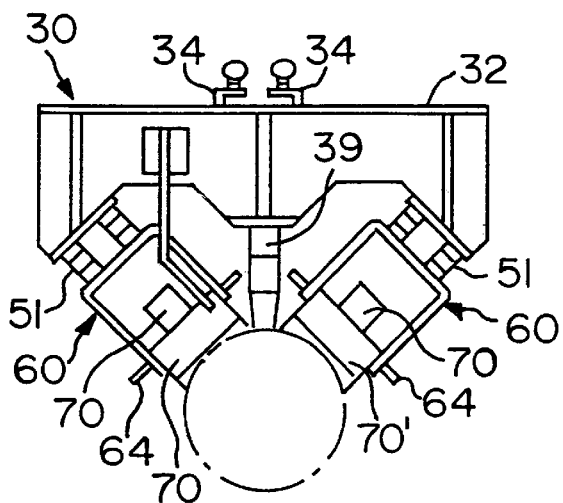

As can be appreciated in FIGS. 3A through 3C, the dimensions of the bracket 32 are varied to accommodate billets of various diameters. For example, a 15" diameter billet requires a bracket 32 having a transverse length of about 30", an 11" diameter billet requires a bracket having a transverse length of about 27" and a 9" diameter billet requires a mounting bracket 32 having a transverse length of about 25¾". In all cases, the transducers 70 of each pair are spaced 90° apart and are perpendicular to the test billet B. By mounting the pair of transducers on the opposed, axially offset wings 33 and 35 of the bracket 32, it will be appreciated that acoustic interference is avoided between the transducers of each pair.

Figure 4:
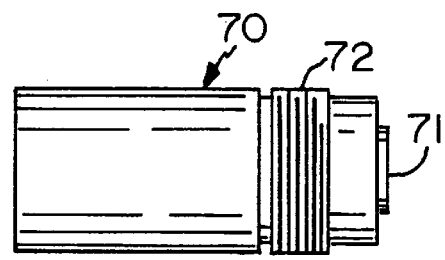
FIG. 4 is a side elevation view of a transducer for use in the present invention.
Figure 7:
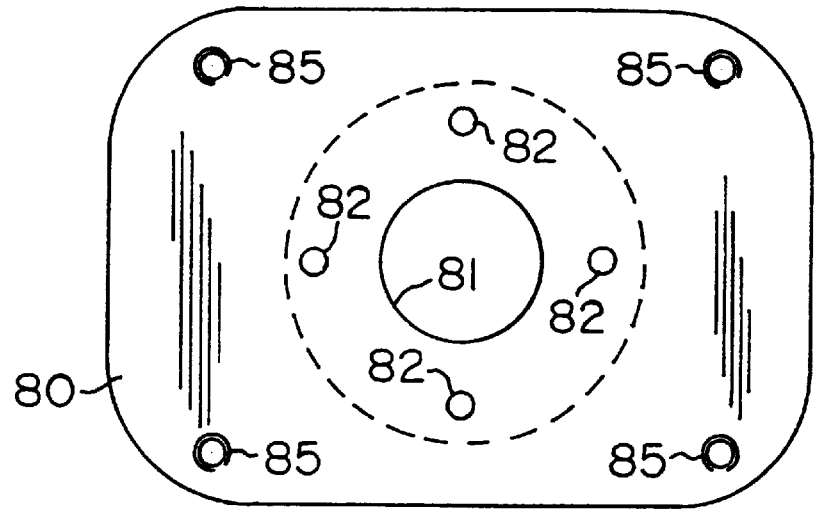
FIG. 7 is a plan view of the holder base of the transducer holder assembly.
Figure 8:
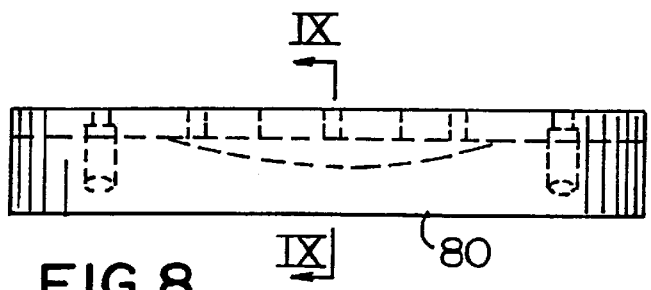
FIG. 8 is a side view of the holder base of FIG. 7.

The transducer 70 shown in FIG. 4 has sound-emitting end 71 and a threaded barrel portion 72. The transducers are housed in the transducer holder assembly or shoe 70' shown in FIGS. 10 and 11. The shoe assembly includes a holder cover 73 shown in FIGS. 5 and 6 for mounting the transducer 70 therein and a base 80, FIGS. 7–9. The holder cover 73 includes a hole 74 with a threaded end to permit the coupling of a source of water or other coupling fluid therein. An annular ring 75 is formed in the holder cover communicating with the hole 74 to permit water to flow within the annular ring 75. An outer annular groove 76 is formed in the cover to receive an O-ring seal to prevent the water from leaking between the holder cover and the holder base 80 depicted in FIGS. 5 through 9. A central bore 77 is provided in the cover 73 with a threaded portion 78 to receive the transducer 70 therein. The threaded section 78, of course, matingly engages the threaded barrel 72 of the transducer. A set screw is positioned within a threaded bore 79 to lockably affix the transducer therein.

The transducer holder base 80 has a central bore 81 formed therein to receive the end 71 of the transducer 70 therethrough. A plurality of holes 82 are formed through the holder base 80 and communicate at their upper ends with the annular water ring 75 formed in the holder cover 73. The holder base has an undercut region 83 shown in FIGS. 9 and 10 which communicates with a lower end of the water holes 82. The lower surface of the holder base 80 has a concave surface 84 having a radius of curvature matching that of the billet being tested. The holder base 80 and holder cover 73 have aligned holes 85 formed therein to permit the holder base 80 to be connected to the cover 73 by way of threaded screws 86 shown in FIG. 11.

Figure 5:
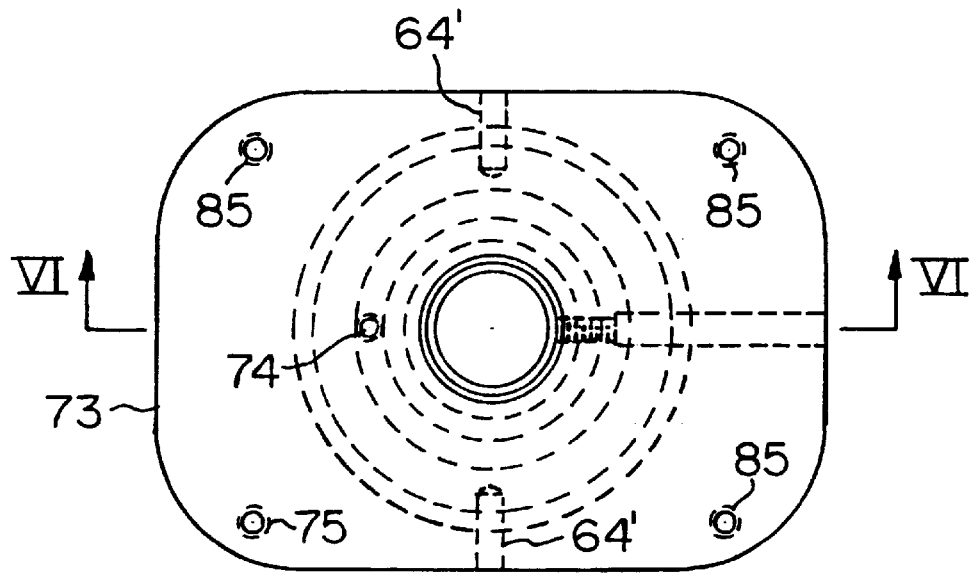
FIG. 5 is a plan view of the transducer holder cover.
Figure 6:
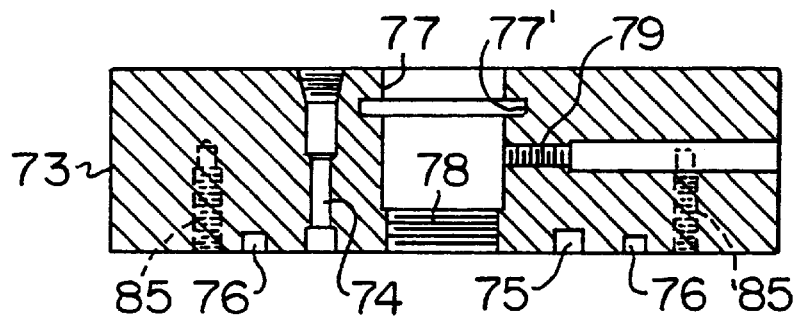
FIG. 6 is a cross sectional view of the holder cover of FIG. 5 taken along line "A—A" thereof.
Figure 10:
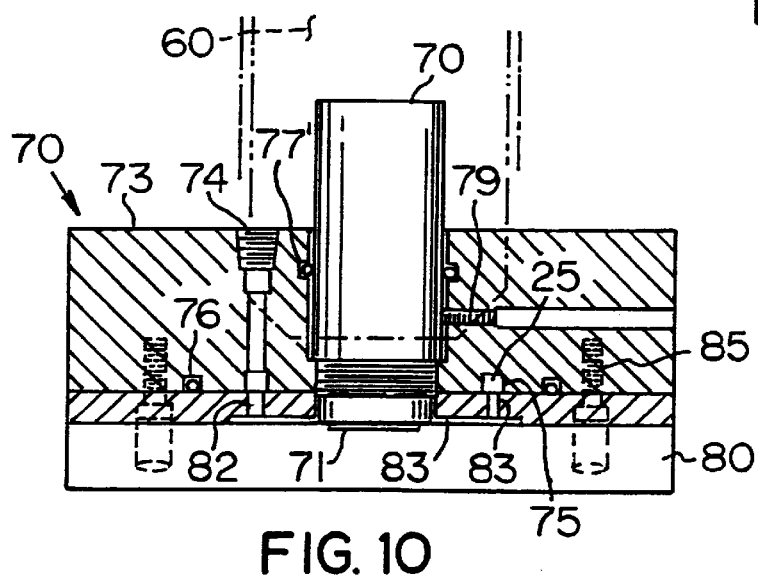
FIG. 10 is a cross sectional view of the transducer holder assembly taken along section line "C—C" of FIG. 11.

With reference to FIGS. 6 and 10, a groove 77' is formed within the bore 77 of the holder cover 73 to accommodate an 0-ring seal to prevent water leakage around the transducer 70. The 0-rings fitting with the grooves 77' and 76 are shown in FIG. 10. The holder cover 73 also has a pair of holes 64' formed on opposed sides thereof as shown in FIG. 5 to receive the mounting bolts 64 therein shown in FIG. 11 for pivotal mounting of the transducer 70 within the bracket 60.

Figure 9:
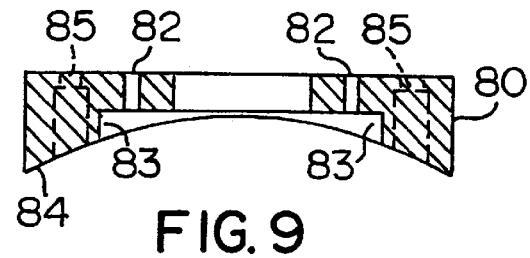
FIG. 9 is a cross sectional view of the holder base taken along section line "B—B" of FIG. 8.

In use, the coupling fluid, such as water, is introduced via a conduit carried by the festoon system into the hole 74 which then floods the annular groove 75 causing water to flow through the holes 82 in the holder base 80 to fill the undercut portion 83 of the holder base. When the curved surface portion 84 engages a billet, the undercut region 83 dams the water therein to form an acoustic coupling pool of fluid between the billet surface and with the end 71 of the transducer 70. The undercut region 83 is a minimum of ⅓₂" at its smallest dimension and extends outwardly a considerable distance (about 0.425") as shown in FIG. 9. The undercut region 83 holds the water within the holder base 80 as the trolley moves along the surface of an as-cast billet to retain the coupling fluid within the undercut region 83, even though the surface of the billet may be rough. The springs 51 are in a compressed state as the guide wheel 39 of the bracket assemblies 32 engages the top surface of the test billet as shown in FIG. 3A. The springs 51 thus forcibly maintain the transducer shoes 70' against the surface of the billet and maintain a sufficient volume of fluid within the undercut region 83 to establish and maintain good acoustic coupling between the transducers and the as-cast billet surface at trolley speeds upwards of 8" per second.

OPERATION

Figure 2A:
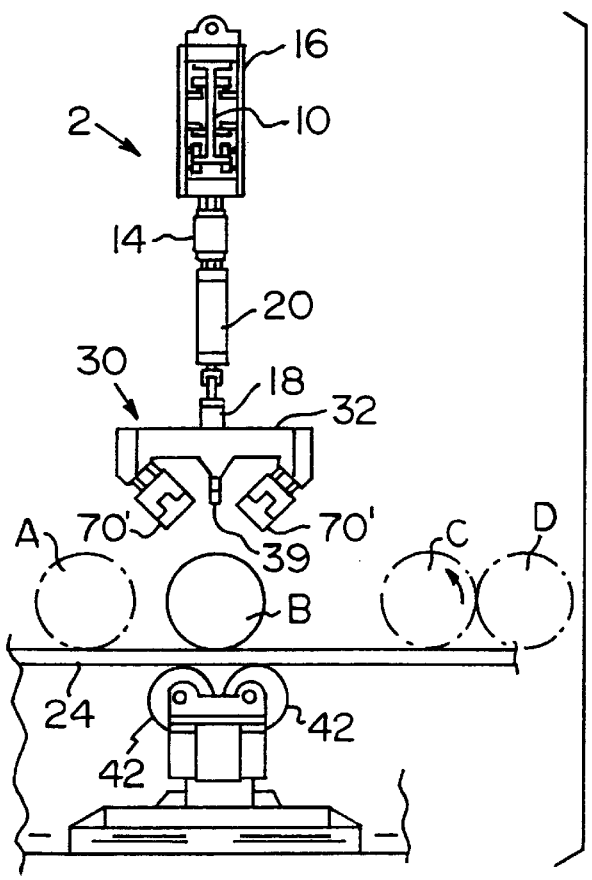
FIGS. 2A–2C depict end views of the inspection apparatus of FIG. 1A showing the sequential movement of the lower rolls to lift the test billet off of the inspection loading rails to a final inspection position shown in FIG. 2C.
Figure 2B:
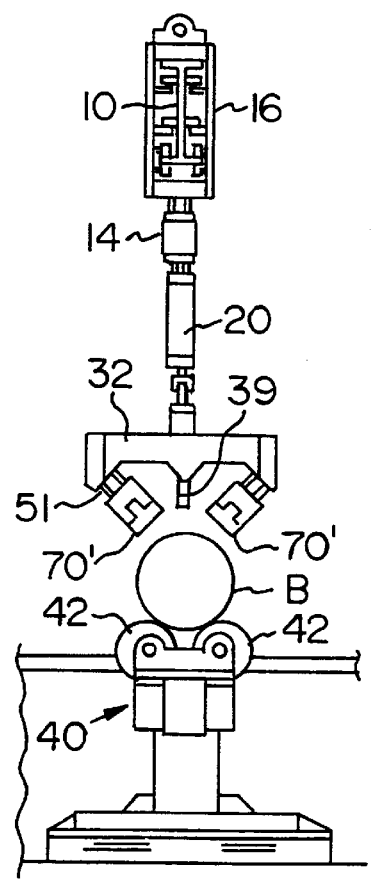
Figure 2C:
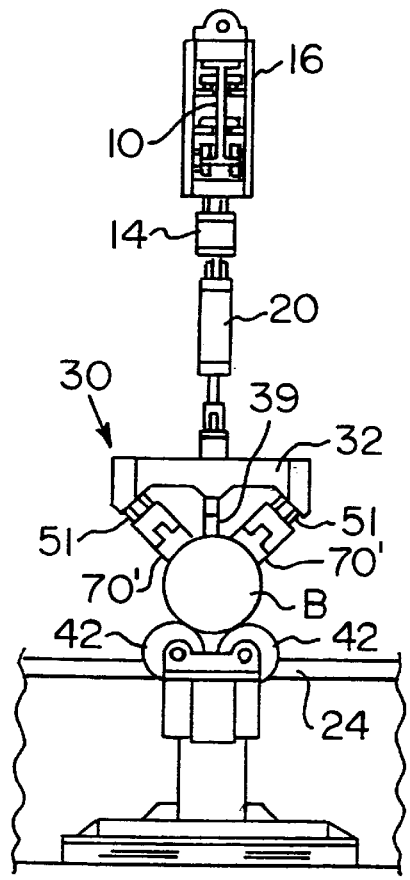

A typical method for ultrasonically inspecting a billet is described hereinafter. The billet B is first rolled along the rails 24 under the bridge beam 10 of the apparatus 2 and manually stopped by the operator. The operator pushes an appropriate control button to activate the cylinders 45 and 45', causing the billet support roller mechanism 40 and 40' to raise from the level shown in FIG. 2A to the level shown in FIG. 2B whereupon the rolls 42 carried by the support mechanism 40 and 40' engage the surface of the billet B. As shown in FIG. 2A, a billet already inspected is identified as "A" and billets to be inspected are indicated as billets "C" and "D". Once the billet B is in position, as in FIG. 2B, the operator pushes an appropriate control mechanism to lower the transducer heads 30 to a position shown in FIG. 2C wherein the shoes 70' of the transducers engage the surface of the billet and the wheel 39 carried by the bracket likewise engages the surface of the billet causing compression of the springs 51. When the transducer assembly 30 moves to the lowered position shown in FIG. 2C, water automatically begins to flow simultaneously. The transducers lower until the shoes 70' contact the billet, for example, at the west end of the billet. The operator shifts a joy stick to rotate the billet clockwise. The joy stick is a momentary contact switch which springs to center if not maintain the clockwise position. When centered, no rotation occurs. The billet will rotate 90° and stop at 90° due to engagement of a billet rotation mechanism as depicted in FIGS. 1A–1G and identified generally by reference numeral 90. A cylinder 92, when activated, causes rotation of a cam 93 and a shaft 94 which causes rotation of the roll 42' to provide selective rotation of the billet B in 90° increments if additional inspection is required.

The operator then pushes a control labeled "flaw inspection speed". This is a selected speed to perform a porosity test on the west end of a billet, adjacent post 4. The operator shifts a joy stick marked "trolley" to the east position. The trolley assembly 12 moves east at a speed of 1" per second, for example. The operator watches an oscilloscope peaks and valleys while the trolley moves east until he sees a total of 12 back reflections. At the point the operator sees 12 back reflections, he releases the joy stick and stops the trolley. This is the point on the west end of the billet that is no longer porous. The operator then manually marks the west end of the billet where the porosity ends. This is where the west end of the billet will be sawed off and discarded due to its porosity. At this stage, the operator is now ready to test the center portion of the billet B for flaws.

The operator then selects and pushes the proper billet inspection speed pushbutton according to the billet size currently being tested. The trolley moves east at one of four possible preselected speeds between 2" per second for large diameter billets up to 6" per second or higher for smaller billet. A first of a pair of photoelectric switches 25 mounted on the transducer bracket 32 reaches the east end of the billet and slows the trolley down to a speed of 1" per second. A second of the pair of photoelectric switches 25 senses the east end of the billet and stops the motor 52 and any further eastward travel. The operator then shifts the joy stick marked "billet rotate" to counterclockwise, if desired, to rotate the billet 90° until the billet rotation cylinder 92 bottoms out. The operator pushes the push-button labeled "flaw detected speed". This is to perform a porosity test on the east end of the billet. The operator shifts the joy stick marked "trolley" to the west position. The trolley then moves west at a speed of 1" per second. The operator watches the oscilloscope peaks and valleys while the trolley moves west until he sees a total of 12 back reflections. As soon as the operator sees 12 back reflections, he releases the joy stick. This is the point on the east end of the billet that is no longer porous which is marked and cut off. The test is now complete for billet B.

The operator then pushes a button labeled "non-inspection fast speed". The operator shifts the joy stick labeled "trolley" to the west position and the trolley moves west at a speed of, for example, 8.75" per second. A photoelectric switch 25' reaches the west end of the billet and slows the trolley down to 1" per second. A second of the pair of photoelectric switches 25' reaches the west end of the billet and stops any further westward traveling. The operator then pushes a push-button labeled "transducer raise" which automatically stops and the transducers 30, 30' raise until the transducer raising cylinders 20, 20' bottom out. The operator then pushes a push-button labeled "billet lower" to lower the rollers 42, 42', 6" to permit the billet B to rest on the mill table beams 24. The billet B is then manually rolled from under the apparatus 2 so the next untested billet C can be rolled onto the apparatus to repeat the inspection sequence described above.

A water collection tray 88 is preferably situated beneath the billet B to collect any excess water which drips from the billet for discard or for recirculation, as desired. An ethylene glycol water mixture can be used in freezing temperatures to prohibit ice formation.

It will be apparent to those of ordinary skill in the art that various changes may be made to the present invention without departing from the spirit and scope thereof. The scope of the present invention is defined by the appended claims and equivalents thereto.

What is claimed is:

1. Apparatus for ultrasonic inspection of an elongated workpiece comprising:
    a) a frame adapted to receive the elongated workpiece;
    b) a trolley means movably attached to the frame for travel along a longitudinal axis of the elongated workpiece;
    c) a first ultrasonic flaw detector means mounted on the trolley means;
    d) a second ultrasonic flaw detector means mounted on the trolley means and axially spaced from said first ultrasonic flaw detector means a distance equal to about one-half of a length of the elongated workpiece;
    e) means for bringing said first and second ultrasonic flaw detector means into acoustic contact with the elongated workpiece such that said first ultrasonic flaw detector means is positioned adjacent a first end of the elongated workpiece and said second ultrasonic flaw detector means is positioned substantially at a mid-point along the length of the elongated workpiece; and
    f) means for moving the trolley means in a first direction along the longitudinal axis of the elongated workpiece to permit ultrasonic testing along an entire length of the elongated workpiece as the trolley means traverses one-half the length of the elongated workpiece.

2. The ultrasonic inspection apparatus of claim 1 wherein the elongated workpiece is cylindrically shaped and wherein the apparatus further includes means for rotating the elongated workpiece upon completion of a traverse by the trolley means whereby a further segment along the entire length of the elongated workpiece may be ultrasonically inspected when the trolley means is moved along the longitudinal axis in a second, opposite direction.

3. The ultrasonic inspection apparatus of claim 2 wherein the first and second ultrasonic flaw detector means each comprise a pair of spaced apart transducers for scanning adjacent 45° quadrants of the workpiece, whereby an entire cross section of the elongated cylindrically shaped workpiece may be ultrasonically inspected in two traverses of the trolley means when the workpiece is rotated after a first traverse.

4. The ultrasonic inspection apparatus of claim 1 wherein the elongated workpiece is a cylindrical metal billet having an irregular as-cast surface, and wherein each of the first and second ultrasonic flaw detector means includes at least one transducer housed in a shoe means, each of said shoe means comprising a body having a concave surface substantially conforming to a surface of the cylindrical billet, said curved surface having an undercut region formed therein and surrounding a sound emitting end of the transducer, said shoe means also having a channel formed therein communicating with the undercut region and adapted to be connected with a source of coupling fluid for supplying a continuous flow of coupling fluid to the undercut region to provide a reservoir to contain the coupling fluid in the undercut region; and wherein each of the first and second ultrasonic flaw detector means further includes biasing means for forcibly urging the curved surface surrounding the undercut region of each of the shoe means into contact with the as-cast surface of the billet so as to increase retention of the coupling fluid in the undercut region of the shoe means, whereby constant acoustic coupling between the transducer and billet is achieved.

5. The ultrasonic inspection apparatus of claim 1 wherein the elongated workpiece is cylindrical in shape and wherein each of the first and second ultrasonic flaw detector means includes bracket means having opposed wing portions extending transverse to the longitudinal axis of the workpiece wherein the wings are axially offset from each other and further including a transducer mounted to an outer end of each of the wing portions, whereby the axial offset mounting of the transducers relative to the longitudinal axis of the workpiece avoids acoustic interference between the pairs of transducers of each of the first and second ultrasonic flaw detector means.

6. Apparatus for ultrasonic inspection of elongated as-cast cylindrical metal billet comprising:

a) a frame adapted to receive the metal billet, b) a trolley means movably attached to the frame for travel along a longitudinal axis of the elongated workpiece;

c) a first ultrasonic flaw detector means mounted on the trolley means, including a first pair of transducers;

d) a second ultrasonic flaw detector means mounted on the trolley means and axially spaced from said first ultrasonic flaw detector means a distance equal to about one-half of a length of the metal billet to be inspected, said second detector means including a second pair of transducers;

e) shoe means for housing each of said transducers comprising a body having a concave surface substantially conforming to a surface of the cylindrical billet, said curved surface having an undercut region formed therein and surrounding a sound emitting end of the transducer, said shoe means also having a channel formed therein communicating with the undercut region and adapted to be connected with a source of coupling fluid for supplying a continuous flow of coupling fluid to the undercut region to provide a reservoir to contain the coupling fluid in the undercut region whereby constant acoustic coupling between the transducer and billet is achieved; and f) means situated below said metal billet for collecting the coupling fluid which may leak from the shoe means and for recycling the coupling fluid.

7. A method for ultrasonically inspecting an elongated workpiece comprising the steps of:

a) providing a trolley means movable along a longitudinal axis of the elongated workpiece;

b) providing first and second ultrasonic flaw detector means on the trolley assembly axially spaced from each other a distance equal to about one-half of a length of the elongated workpiece;

c) bringing said first and second ultrasonic flaw detector means into acoustic contact with the elongated workpiece such that said first ultrasonic flaw detector means is positioned adjacent a first end of the elongated workpiece and said second ultrasonic flaw detector means is positioned substantially at a mid-point along the length of the elongated workpiece; and d) moving the trolley means in a first direction along the longitudinal axis of the elongated workpiece to permit ultrasonic testing along an entire length of the elongated workpiece as the trolley means traverses one-half the length of the elongated workpiece.

8. The method of claim 7 including the step of providing means for rotating the elongated workpiece upon completion of a traverse by the trolley means whereby a further segment along the entire length of the elongated workpiece may be ultrasonically inspected when the trolley means is moved along the longitudinal axis in a second, opposite direction.

9. The method of claim 7 including the step of supplying a coupling fluid to the first and second ultrasonic flaw detector means.

10. The method of claim 9 including the steps of providing shoe means having an undercut region for retaining said coupling fluid and forcibly urging said shoe means into contact with a surface of the elongated workpiece as the trolley means traverses the workpiece to increase retention of the coupling fluid in the undercut region.

* * * * *

UNITED STATES PATENT AND TRADEMARK OFFICE
CERTIFICATE OF CORRECTION

PATENT NO. : 5,948,985
DATED : September 7, 1999
INVENTOR(S) : David R. Brautigan et al.

It is certified that error appears in the above-identified patent and that said Letters Patent is hereby corrected as shown below:

Column 1 Line 32 "such-as cast" should read --such as-cast--.

Column 2 Line 38 "soundemitting" should read --sound-emitting--.

Column 5 Line 34 "springloaded" should read --spring-loaded--.

Column 6 Line 22 "0-ring" should read --O-ring--.

Column 6 Line 23 "0-rings" should read --O-ring--.

Column 7 Line 35 "pushbutton" should read --push-button--.

Column 9 Line 1, Claim 4, "sound emitting" should read
--sound-emitting--.

Column 9 Line 46, Claim 6(e), "sound emitting" should read
--sound-emitting--.

Signed and Sealed this

Second Day of May, 2000

Attest:

Attesting Officer

Q. TODD DICKINSON

Director of Patents and Trademarks